United States Patent [19]
Portney

[11] Patent Number: 5,225,858
[45] Date of Patent: Jul. 6, 1993

[54] MULTIFOCAL OPHTHALMIC LENS

[76] Inventor: Valdemar Portney, 7 Alassio, Irvine, Calif. 92720

[21] Appl. No.: 717,336

[22] Filed: Jun. 18, 1991

Related U.S. Application Data

[60] Continuation-in-part of Ser. No. 465,477, Jan. 16, 1990, Pat. No. 5,166,712, which is a division of Ser. No. 366,319, Jun. 14, 1989, Pat. No. 4,898,461, which is a continuation of Ser. No. 56,050, Jun. 1, 1987, abandoned.

[51] Int. Cl.$^5$ .................. G02C 7/04; A61F 2/14; A61F 2/16
[52] U.S. Cl. ........................... 351/161; 623/5; 623/6
[58] Field of Search ............... 351/160 R, 160 H, 161, 351/162; 623/6, 5

[56] References Cited

U.S. PATENT DOCUMENTS

| | | | |
|---|---|---|---|
| Re. 25,286 | 11/1962 | DeCarle | 351/161 |
| 1,483,509 | 2/1924 | Bugbee | 351/168 |
| 2,129,305 | 9/1938 | Feinbloom | 351/160 R |
| 2,274,142 | 2/1942 | Houchin | 351/168 |
| 2,405,989 | 8/1946 | Beach | 351/169 |
| 2,511,517 | 6/1950 | Spiegel | 351/169 |
| 3,004,470 | 10/1961 | Ruhle | 351/168 |
| 3,031,927 | 5/1962 | Wesley | 351/161 |
| 3,034,403 | 5/1962 | Neefe | 351/162 |
| 3,210,894 | 10/1965 | Bentley | 51/284 R |
| 3,227,507 | 1/1966 | Feinbloom | 351/160 R |
| 3,339,997 | 9/1967 | Wesley | 351/161 |
| 3,420,006 | 7/1969 | Barnett | 351/129 |
| 3,431,327 | 3/1969 | Tsuetaki | 351/161 |
| 3,482,906 | 12/1969 | Volk | 351/160 R |
| 3,542,461 | 11/1970 | Girard et al. | 351/160 H |
| 3,693,301 | 9/1972 | Lemaltre | 51/284 R |
| 3,794,414 | 2/1974 | Wesley | 351/161 |
| 3,932,148 | 1/1976 | Krewalk, Sr. | 51/284 R |
| 4,055,378 | 10/1977 | Feneberg et al. | 351/160 H |
| 4,062,629 | 12/1977 | Winthrop | 351/169 |
| 4,073,579 | 2/1978 | Deeg et al. | 351/169 |
| 4,162,122 | 7/1979 | Cohen | 351/161 |
| 4,195,919 | 4/1980 | Shelton | 351/160 R |
| 4,199,231 | 4/1980 | Evans | 351/160 H |
| 4,210,391 | 7/1980 | Cohen | 351/161 |
| 4,240,719 | 12/1980 | Guilino et al. | 351/169 |
| 4,274,717 | 6/1981 | Davenport | 351/169 |
| 4,307,945 | 12/1981 | Kitchen et al. | 351/169 |
| 4,315,673 | 2/1982 | Guilino et al. | 351/169 |
| 4,338,005 | 7/1982 | Cohen | 351/161 |
| 4,340,283 | 7/1982 | Cohen | 351/161 |
| 4,377,329 | 3/1983 | Poler | 351/160 R |
| 4,402,579 | 9/1983 | Poler | 351/160 R |
| 4,418,991 | 12/1983 | Breger | 351/161 |
| 4,504,982 | 3/1985 | Burk | 623/6 |

(List continued on next page.)

FOREIGN PATENT DOCUMENTS

| | | |
|---|---|---|
| 32257/89 | 10/1989 | Australia . |
| 159395 | 12/1914 | Canada . |
| 0140063 | 5/1985 | European Pat. Off. . |
| 0351471 | 1/1990 | European Pat. Off. . |
| 2702117 | 7/1978 | Fed. Rep. of Germany . |

(List continued on next page.)

OTHER PUBLICATIONS

Mandell, R. B.; Contact Lens Practice; Charles C. Thomas, Publisher; Springfield, Ill.; pp. 385, 211–212, 403–404, 491–492, 792, 819.

Encyclopedia of Contact Lens Practice; Chapter 23; Sep. 1, 1960; pp. 24–26.

(List continued on next page.)

Primary Examiner—Scott J. Sugarman
Attorney, Agent, or Firm—Gordon L. Peterson

[57] ABSTRACT

A multifocal ophthalmic lens adapted for implantation in the eye or to be disposed on or in the cornea. The lens has an optical axis, a central zone and a plurality of annular zones circumscribing the central zone. Two of the annular zones have a first region with a far vision correction power and a second region with a near vision correction power. In an IOL embodiment, the vision correction power between far and near is progressive, and each of the second regions has a major segment in which the near vision correction power is substantially constant. The power in the central zone varies.

34 Claims, 9 Drawing Sheets

U.S. PATENT DOCUMENTS

| | | | |
|---|---|---|---|
| 4,573,775 | 3/1986 | Bayshore | 351/161 |
| 4,580,882 | 4/1986 | Nuchman et al. | 351/161 |
| 4,596,578 | 6/1986 | Kelman | 623/6 |
| 4,618,228 | 10/1986 | Baron et al. | 351/161 |
| 4,618,229 | 10/1986 | Jacobstein et al. | 351/161 |
| 4,636,049 | 1/1987 | Blaker | 351/161 |
| 4,636,211 | 1/1987 | Nielsen et al. | 351/161 |
| 4,637,697 | 1/1987 | Freeman | 351/161 |
| 4,641,934 | 2/1987 | Freeman | 351/160 R |
| 4,693,572 | 9/1987 | Tsuetaki et al. | 351/161 |
| 4,704,016 | 11/1987 | de Carle | 351/161 |
| 4,720,286 | 1/1988 | Bailey et al. | 623/6 |
| 4,752,123 | 6/1988 | Blaker | 351/161 |
| 4,759,762 | 7/1988 | Grendahl | 623/6 |
| 4,769,033 | 9/1988 | Nordan | 623/6 |
| 4,795,462 | 1/1989 | Grendahl | 623/6 |
| 4,813,955 | 3/1989 | Achatz et al. | 623/6 |
| 4,830,481 | 5/1989 | Futhey et al. | 351/161 |
| 4,881,804 | 11/1989 | Cohen | 351/161 |
| 4,890,912 | 1/1990 | Visser | 351/161 |
| 4,890,913 | 1/1990 | DeCarle | 351/161 |
| 4,898,461 | 2/1990 | Portney | 351/161 |
| 4,917,681 | 4/1990 | Nordan | 623/6 |
| 4,919,663 | 4/1990 | Grendahl | 623/6 |
| 4,921,496 | 5/1990 | Grendahl | 623/6 |
| 4,923,296 | 5/1990 | Erickson | 351/161 |
| 4,938,583 | 7/1990 | Miller | 351/161 |
| 5,000,559 | 3/1991 | Takahashi et al. | 351/169 |
| 5,002,382 | 3/1991 | Seidner | 351/161 |
| 5,019,099 | 5/1991 | Nordan | 623/6 |
| 5,096,285 | 3/1992 | Silberman | 351/161 |
| 5,112,351 | 5/1992 | Christie et al. | 623/6 |

FOREIGN PATENT DOCUMENTS

| | | |
|---|---|---|
| 253097 | 1/1988 | German Democratic Rep. . |
| 89/02251 | 3/1989 | PCT Int'l Appl. . |
| 89/11672 | 11/1989 | PCT Int'l Appl. . |
| 90/00889 | 2/1990 | PCT Int'l Appl. . |
| 888414 | 11/1988 | South Africa . |
| 939016 | 10/1963 | United Kingdom . |
| 2058391A | 4/1981 | United Kingdom . |
| 2129155A | 5/1984 | United Kingdom . |
| 2146791A | 4/1985 | United Kingdom . |
| 2192291 | 1/1988 | United Kingdom . |
| WO86/03961 | 7/1986 | World Int. Prop. O. . |
| WO87/00299 | 1/1987 | World Int. Prop. O. . |
| WO87/07496 | 12/1987 | World Int. Prop. O. . |

OTHER PUBLICATIONS

DeCarle, J. T.; *"Further Developments of Bifocal Contact Lenses"*; Contacto; Jun. 1966; pp. 185-186.

"The Shah Bifocal Intraocular Lens Implant", Shah & Shah Intraocular Lens Laboratories, Calcutta, India (Book).

"Lens Design Fundamentals"; R. Kingslake; Institute of Optics University of Rochester, Rochester, N.Y.; Academic Press 1978 (Book) pp. 36-39.

"A Three-Part System For Refining Intraocular Lens Power Calculations", *Journal of Cataract and Refractive Surgery*, J. T. Holladay, M.D., et al, vol. 14, Jan. 1988, pp. 17-23.

Video Tape "ASCRS-ASOA Design of Aspheric Multifocal Intraocular Lens Clinical Relevance", Lee T. Nordan, Mar. 6, 1960 (in file).

Transcript of Nordan Video Tape.

Ocular Surgery News, "Multifocal IOLs: Are they ophthalmology's next revolution in visual rehabilitation?", 6 pages, Jan. 15, 1989.

Ioptex Research Inc., "Evaluation of Optical Designs for Multifocal Intraocular Lenses" (Book).

"Video Tape of ASCRS Session VIII, Design Optimization Of The Aspheric Multifocal IOL", Dr. Russell Chipmen, Ph.D., Mar. 6, 1990 (in file).

Transcript of Video Tape entitled "The Design Optimization Of The Aspheric Multifocal IOL," Dr. Russell Chipmen, Ph.D.

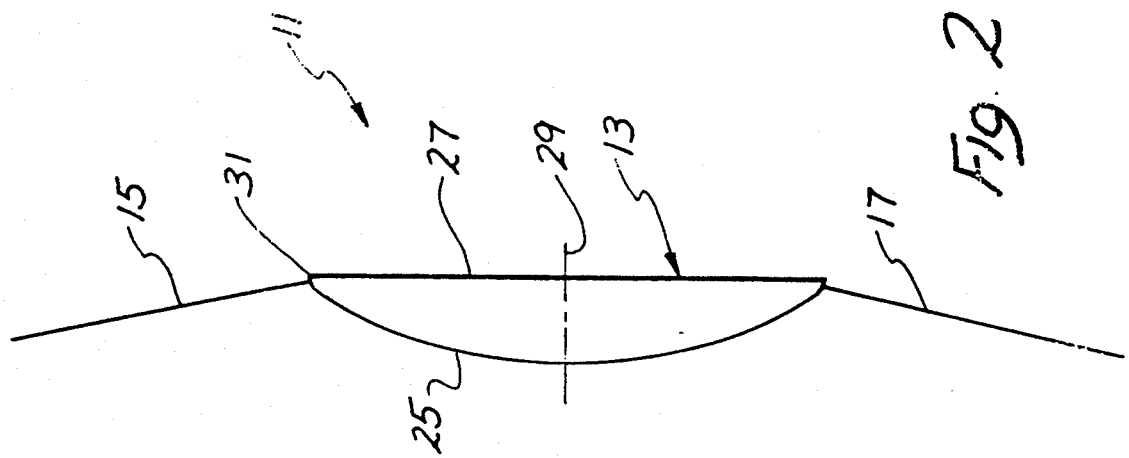
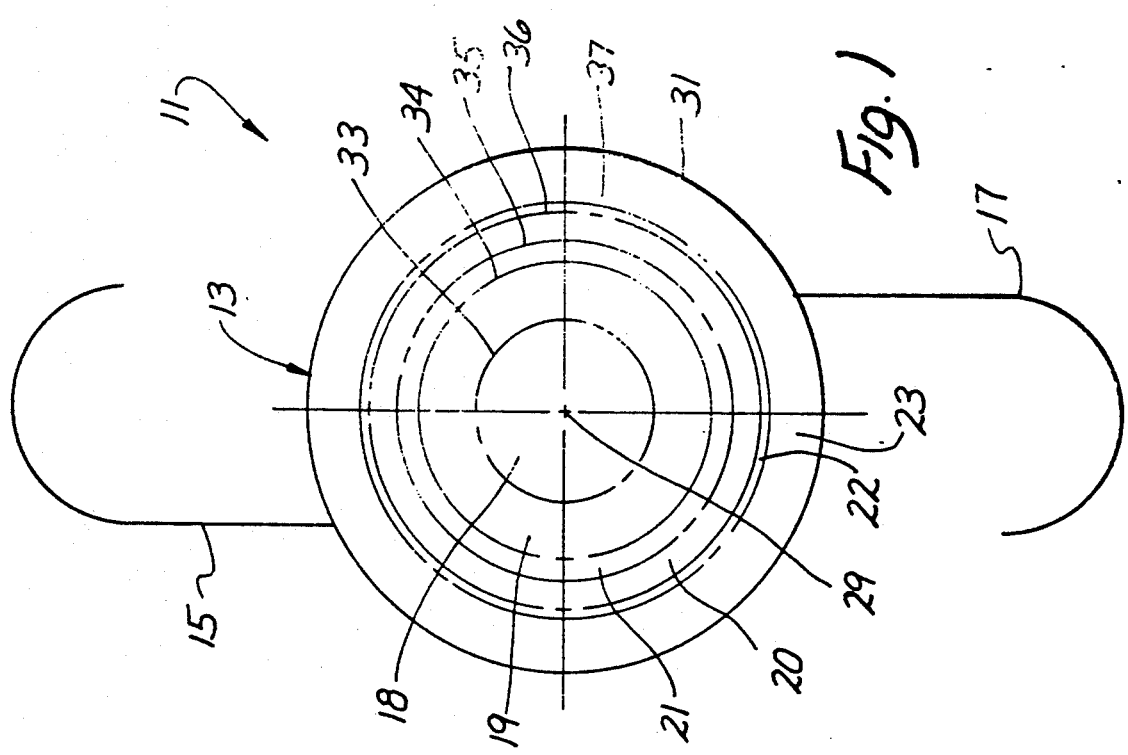

MULTIFOCAL OPHTHALMIC LENS

This application is a continuation in part of application Ser. No. 465,477 filed on Jan. 16, 1990 now U.S. Pat. No. 5,166,712 which is a division of application Ser. No. 366,319 filed Jun. 14, 1989 now U.S. Pat. No. 4,898,461, which is a continuation of Ser. No. 56,050 filed Jun. 1, 1987, now abandoned.

BACKGROUND OF THE INVENTION

This invention relates to a multifocal ophthalmic lens and in particular to a lens adapted for implantation in an eye, such as an intraocular lens (IOL), or to be disposed on or in the cornea, such as a contact lens, corneal onlay or corneal inlay. The corneal inlay may also be regarded as an implant.

A specific embodiment shown in my U.S. Pat. No. 4,898,461 (which patent is incorporated by reference herein) discloses a multifocal ophthalmic lens which includes a central zone circumscribed by multiple concentric, annular zones. The central zone may have a vision correction power for intermediate correction and from there the vision correction power varies progressively in a radial outward direction to a far vision correction power, and then to a near vision correction power. In the specific embodiment of this patent, the progressive vision correction power is varied between far and near through the several zones.

A multifocal ophthalmic lens of this type provides multiple images on the retina. One or more of these images is in focus and one or more of these images is out of focus. The human brain selects the in-focus image to enable a multifocal ophthalmic lens of this type to function well at near, intermediate and far viewing distances.

SUMMARY OF THE INVENTION

For given lighting conditions, there is only a fixed amount of light that will pass through a lens to the retina. This invention utilizes a multifocal lens to distribute the light most effectively among near, intermediate and far images.

In terms of viewing distances, far is often regarded as the most important because good far vision is required for certain tasks, such as driving, where safety is important. Also, when viewing an object at a far viewing distance, lighting conditions and distance to the object often cannot be altered. Near vision is very important for reading and other close work. However, near vision is often needed under circumstances where light intensity can be increased and viewing distance altered, if needed. Finally, intermediate images are generally least important.

A multifocal lens can be designed to have an increased depth of focus, but this reduces image quality. Conversely, image quality can be increased at the expense of depth of focus. A feature of this invention is to increase depth of focus in certain portions of the lens and to provide maximum image quality in other portions of the lens and to locate the high depth of focus and high image quality portions of the lens in a way to enhance vision for far, near and intermediate objects.

One aspect of this invention is to provide improved image quality and light intensity for near images. This can be accomplished by maintaining the near vision correction power of appropriate zones of the lens substantially constant for a major segment of the near vision correction power region of each zone and by providing a central zone having an increased depth of focus.

For near vision, the working distance, i.e., the distance between the eye and the object, can usually be varied with relative ease as when a person reading adjusts the distance between his eyes and the material being read. For this reason, it is desirable to concentrate as much light as possible at a single near location to provide maximum image quality at such near location This is accomplished by the major segments of each near vision correction power region which have substantially constant near vision correction power. Although this inherently reduces the depth of focus at such major segments, this is typically immaterial at this near location because of the ability to easily adjust the working distance. Although this feature is useful in contact lenses, corneal onlays and corneal inlays, it is particularly applicable to an intraocular lens (IOL) because, in that instance, the patient has minimal residual accommodation, i.e., the ability of a normal eye to see objects at different distances.

As explained more fully below, it is desirable to space the near vision correction power regions radially outwardly from the central zone of the lens. This can be accomplished by providing the multifocal ophthalmic lens with a plurality of annular zones circumscribing an optical axis with each of first and second of the annular zones having a far vision correction power and a region with a near vision correction power. The vision correction power between the far and near vision correction powers is progressive. Each of the regions has a major segment in which the near vision correction power is substantially constant. This provides improved image quality and light intensity for near images and less intensity for intermediate images where image quality is of less importance.

This invention is generally applicable to a multifocal ophthalmic lens of the type which is adapted to be implanted in an eye, such as an IOL or disposed on or in the cornea, such as a contact lens, a corneal onlay or a corneal inlay. A multifocal lens of this type has a reduced depth of focus as compared with a monofocal lens. This reduction in depth of focus is particularly noticeable for a multifocal intraocular lens because, as indicated above, the patient has only minimal residual accommodation. Another feature of this invention is to increase the depth of focus of the central zone of the multifocal ophthalmic lens. This invention employs several concepts, which can be used separately or in combination to increase the depth of focus of the central zone of the lens.

First, the depth of focus is related to the aperture or pupil size, and a smaller pupil provides a larger depth of focus. For example, for a 2 millimeter diameter pupil, there is a depth of focus of about 2 diopters or more. In bright light, the pupil of the human eye is typically approximately 2 millimeters in diameter. To take advantage of this inherent depth of focus obtainable by a relatively small aperture, the central zone of an IOL constructed in accordance with this invention is preferably, but not necessarily, about 2 to 2.1 millimeters in diameter. Because of the effective optical zone size at the location of a contact lens, the central zone of a contact lens constructed in accordance with this invention is preferably, but not necessarily, about 2.25 mm in diameter. In addition, this invention preferably includes additional features which increase the depth of focus of the central zone beyond that provided by the relatively small-diameter central zone. For example, these other features may increase the depth of focus of the central zone about 1 diopter. With this arrangement, the central zone has about a 3 diopter depth of focus, and typically this is sufficient for near vision even if no near vision correction power is provided in the central zone.

With this invention, the depth of focus of the central zone is extended by controlling the vision correction power of the central zone. One way to accomplish this is to provide a negative diopter vision correction power in the central zone. The negative diopter vision correction power is negative with respect to a baseline power which, for purposes of definition, is regarded as a 0 diopter power. The baseline diopter power is the power required to provide far vision correction power for the patient. The negative diopter power is less than the baseline diopter power and is a negative diopter power in the sense that it is less than, or negative with respect to, the baseline power. The negative diopter power may also be considered as a far, far vision correction power.

In addition to employing the negative diopter vision correction power in the central zone, the central zone also includes progressive vision correction powers to further extend the depth of focus of the central zone.

In a preferred construction of this invention, the central zone has, in radially outwardly extending order, an intermediate vision correction power, a far vision correction power and a negative diopter power in a peripheral region of the central zone. With this arrangement, the rays at the periphery of the central zone are directed to far, far focal points where they have less impact on the depth of focus. Consequently, the depth of focus is increased over a conventional monofocal lens of the type adapted to be implanted in the eye or worn on a surface of the eye. The increased depth of focus feature, although advantageous for certain contact lens applications, is particularly advantageous for intraocular lenses because of the loss of accommodation resulting from removal of the natural lens of the eye.

Preferably the vision correction power of the central zone is continuously variable or progressive. This provides intermediate dioptric powers in several locations on the surface of the lens. The intermediate correction power is the greatest diopter power of the central zone. The central zone is circumscribed by one or more outer annular zones, each of which preferably has near and far vision correction powers.

Preferably, the central zone has a far, far vision correction power at the optical axis. In addition to increasing depth of focus, the far, far vision correction power compensates for the presence of the intermediate vision correction powers in the central zone so that the central zone will have a mean power equal to the far vision correction power for the patient.

Accordingly, by employing the depth of focus features at the central zone of the lens, the central zone can be typically used for near vision in bright light conditions. In addition, the central zone contains the patient's prescription for far vision so far objects can also be viewed in bright viewing conditions.

As light diminishes and pupil size correspondingly increases, near vision correction power is provided by the annular zones referred to above which have the capability of providing high quality near images. Thus, this invention takes advantage of both depth of focus and image quality features to provide for enhanced multifocal viewing of near objects for various pupil sizes, i.e., various lighting conditions.

It is also desired to provide for far vision correction at locations radially outwardly of the central zone. For this purpose, the multifocal lens preferably has a third annular zone extending between the first and second annular zones. The third annular zone has a vision correction power which is less than the near vision correction power throughout the full radial dimension of the third annular zone. This vision correction power may include a far or far, far vision correction power. With this arrangement, far vision correction power is provided in the central zone for viewing of far objects under bright-light conditions and in one or more zones spaced radially outwardly of the central zone to provide for the viewing of far objects under less bright lighting conditions.

This invention also provides for a vision correction power which varies in a way to reduce aberrations in each far vision correction portion and each near vision correction portion. This is particularly important for contact lenses.

To reduce aberrations, the diopter power for each far vision correction portion and the diopter power for each near vision correction portion of the lens is continuously reduced in a radial outward direction. As a result, the image quality for far and near images is maximized.

In a preferred embodiment, the lens has multiple annular zones with the vision correction power in each of the zones increasing in a radial outward direction relatively rapidly from a far vision correction power to a maximum near vision correction power, then decreasing in a radial outward direction more slowly during a major segment of a near vision region and then decreasing in a radial outward direction more rapidly to a far vision correction power. Preferably the vision correction power of each of the near vision regions reduces generally linearly from the maximum near vision correction power so as to reduce the aberrations. It is the reduction of the vision correction power of each of the near vision regions as such regions extend radially outwardly which serves to reduce the aberrations.

A similar vision power correction throughout the regions having far vision correction powers is used to reduce spherical aberrations of such far regions. Thus, the third annular zone between the first and second annular zones has far vision correction powers which decrease for a distance from the first annular zone radially outwardly. Likewise, the central zone also may have vision correction powers which decrease radially outwardly in at least a portion of the central zone to minimize spherical aberrations in such zone.

The desired power for the lens can be provided in various different ways, including the use of refracting surfaces. In one preferred embodiment, the lens has anterior and posterior surfaces, at least one of which is shaped to provide the desired vision correction powers. With this construction, the progressive portions of the lens are aspheric, and although the regions of the lens of constant power can be spheric if desired, preferably they are also aspheric. It is possible to employ an aspheric surface to generate a region of constant power because the refractive properties of a surface depend, not only upon the radius of the surface, but also on the location of the center of the radius. In a preferred construction, the lens of this invention is aspheric throughout the annular zones and the central zone, and this provides certain advantages in designing the lens and also can be used to compensate for spherical aberrations for far vision portions and near vision portions of the lens.

For a contact lens, it is preferred to shape the posterior surface to fit the curvature of the patient's eye and to configure the anterior surface to provide the desired correction. Regardless of how the vision correction powers are provided, a contact lens can be designed to be more progressive to avoid having two relatively clear images but at some sacrifice in image quality. Alternatively, a contact lens can be designed to provide maximum image quality for both near and far objects, but in this event, blending is compromised. These alternatives provide a wider range of choice for suiting each patient's particular needs.

The invention, together with additional features and advantages thereof, may best be understood by reference to the following description taken in connection with the accompanying illustrative drawing.

BRIEF DESCRIPTION OF THE DRAWING

FIG. 1 is a plan view of an IOL embodying the features of this invention.

FIG. 2 is a side elevational view of the IOL.

DESCRIPTION OF THE PREFERRED EMBODIMENT

Figure 3:
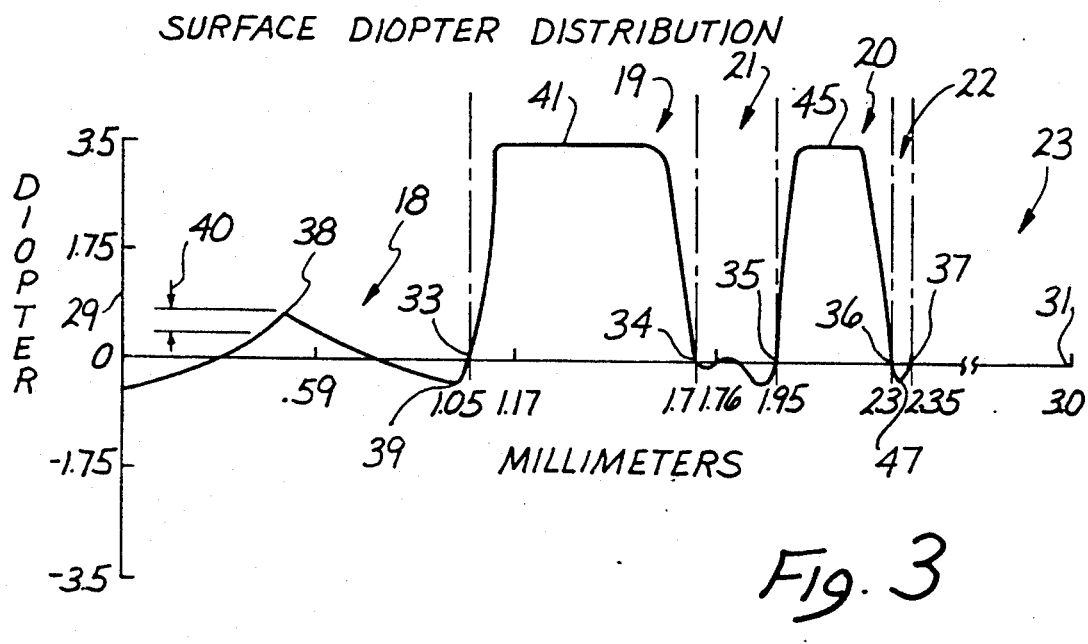
FIG. 3 is a plot of the power of the optic versus distance from the optical axis for the IOL.

FIGS. 1 and 2 show an intraocular lens 11 which comprises a circular optic 13 and fixation members 15 and 17. The optic 13 may be constructed of rigid biocompatible materials, such as polymethylmethacrylate (PMMA), or flexible, deformable materials, such as silicone, hydrogel and the like which enable the optic to be rolled or folded for insertion through a small incision into the eye.

In this embodiment, the fixation members 15 and 17 are fine hair-like strands or filaments which are attached to the optic 13 using conventional techniques. The fixation members 15 and 17 may be constructed of a suitable polymeric material, such as PMMA or polypropylene. Alternatively, the fixation members 15 and 17 may be integral with the optic 13. The optic 13 and the fixation members 15 and 17 may be of any desired configuration, and the configurations illustrated are purely illustrative.

The optic 13 has a central zone 18, inner and outer annular near zones 19 and 20 and annular far zones 21, 22 and 23. In this embodiment, the central zone 18 is circular and the peripheries of the annular zones 19-23 are circular. The annular zones 19-23 circumscribe the central zone 18, and the zones are contiguous. The zones 19-23 are concentric and coaxial with the optic 13.

The zones 18-23 are used in describing the vision correction power of the optic 13, and they are arbitrarily defined. Thus, the peripheries of the zones 18-22 and the number of zones may be selected as desired. However to facilitate describing the optic 13, the peripheries of the annular zones 19-22 are considered to be the major zero crossings in FIG. 3. Although the boundaries of the zones 18-23 are indicated by phantom lines in FIG. 1, it should be understood that the optic 13 has no such lines in any of its surfaces and that these lines constitute reference lines which define the zones.

In the embodiment of FIG. 2, the optic 13 has a convex anterior surface 25 and a planar posterior surface 27; however, these configurations are merely illustrative. Although the vision correction power may be placed on either of the surfaces 25 or 27, in this embodiment, the anterior surface 25 is appropriately shaped to provide the desired vision correction powers.

FIG. 3 shows the preferred manner in which the vision correction power of the optic 13 varies from the center or optical axis 29 of the optic to the circular outer periphery 31 of the optic. A preferred power distribution curve for a corneal inlay may be similar, or identical, to the curve of FIG. 3. In FIG. 3, the vertical or "Y" axis represents the variation in diopter power of the optic 13 from the baseline or far vision correction power, and the "X" or horizontal axis shows the distance outwardly from the optical axis 29 in millimeters. Thus, the zero-diopter or baseline power of FIG. 3 is the power required for far vision for an IOL. The power variation shown in FIG. 3 is applicable to any radial plane passing through the optical axis 29. In other words, the power at any given radial distance from the optical axis 29 is the same.

The central zone 18 extends from the optical axis 29 to a circular periphery 33, the inner annular near zone 19 is considered as extending from the periphery 33 to a circular periphery 34, and the outer annular near zone is considered as extending from a periphery 35 to a periphery 36. The annular far zone 21 extends between the peripheries 34 and 35, and the annular far zone 22 extends from the periphery 36 radially outwardly to a periphery 37. The annular zone 23 extends from the periphery 37 radially outwardly to the outer periphery 31 of the optic 13. As shown in FIG. 3, the vision correction power crosses the "X" axis or baseline at the peripheries 33, 34, 35, 36 and 37. The crossings of the baseline in the zone 21 are considered minor and do not define any zone boundary.

As shown in FIG. 3, the vision correction power varies progressively and continuously from a negative diopter power at the optical axis 29 through a baseline diopter correction power to an apex 38 and then decreases continuously and progressively from the apex 38 back through the baseline diopter correcfion to another negative diopter power at a point 39. The negative diopter powers at the optical axis and the point 39 are of less power than is required for far vision and may be considered as far, far vision correction powers. From the point 39, the vision correction power increases continuously and progressively through the periphery 33 into the inner annular near zone 19. Of course, the diopters shown on the ordinate in FIG. 3 are merely exemplary, and the actual correction provided will vary with the prescription needs of the patient.

The apex 38 has a vision correction power for intermediate vision. The intermediate vision correction powers may be considered as being in a zone 40 which may be between 0.5 and 0.75 diopters from the baseline diopter power. The far vision correction powers may be considered as lying between the zone 40 and the baseline diopter correction, and the far, far vision correction powers are negative. The intermediate, far and far, far powers combine to provide a mean power in the central zone 18 for far vision.

Within the inner annular near zone 19, the vision correction power varies continuously and progressively from the periphery 33 to a plateau 41, and from the plateau, the vision correction power varies continuously and progressively back to the periphery 34 at the baseline. In the far zone 21, the vision correction power increases very slightly above the baseline and then proceeds to a far, far negative vision correction power at a point 43 at which the vision correction power reverses and returns to the baseline at the periphery 35.

In the outer annular near zone 20, the power varies continuously and progressively from the periphery 35 to a plateau 45 and returns continuously and progressively from the plateau 45 to the baseline at the periphery 36. In the far zone 22, the power dips slightly below the baseline to a point 47 in the far, far correction region and then returns to the baseline at the outer periphery 37. The dips below the baseline to the points 43 and 47 in the far zones 21 and 22 help support the increased depth of focus of the central zone 18.

The far zone 23 has a vision power that lies along the baseline and is configured for far vision. The zone 23, which lies radially outwardly of a diameter of 4.7 mm, is only usable in poor light conditions when the pupil is very large. Under poor lighting conditions such as this, far vision is all that is normally required.

The inner near zone 19 has regions adjacent the peripheries 33 and 34 with far vision correction powers and a second region, which includes the plateau 41 with near vision correction powers. Similarly, the outer near zone 20 has regions adjacent the peripheries 35 and 36 with far vision correction powers and a second region, which includes the plateau 45, with near vision correction powers. For example, the near vision powers may be those which are above 2 or 2.5 diopters. The 2 to 2.5 diopters correspond to about 20 to 15 inches, respectively, of working distance, and this distance corresponds to the beginning of near activities.

As shown in FIG. 3, each of these "near" regions has a major segment, i.e., the plateaus 41 and 45 in which the near vision correction power is substantially constant. The plateau 41, which lies radially inwardly of the plateau 45, has a greater radial dimension than the plateau 45. The difference in radial dimensions of the plateaus 41 and 45 allows these two plateaus to have approximately the same area.

Only a relatively small portion of the anterior surface 25 is dedicated to intermediate vision powers. This can be seen by the relatively small radial region which corresponds to the intermediate zone 40 (FIG. 3) and by the rapid change in diopter power between the plateaus 41 and 45 and the baseline diopter axis. Consequently, as explained more fully hereinbelow, a relatively small portion of the light intensity is dedicated to intermediate images.

It can be seen from FIG. 3 that the vision correction power of the central zone is continuously variable and that the vision correction power of the entire optic, except for the plateaus 41 and 45, is continuously variable. The apex 38 is the greatest diopter power of the central zone 18, and the negative diopter power at the optical axis 29 and the points 39, 43 and 47 is blended smoothly with the vision correction powers radially outwardly thereof.

Figure 4:
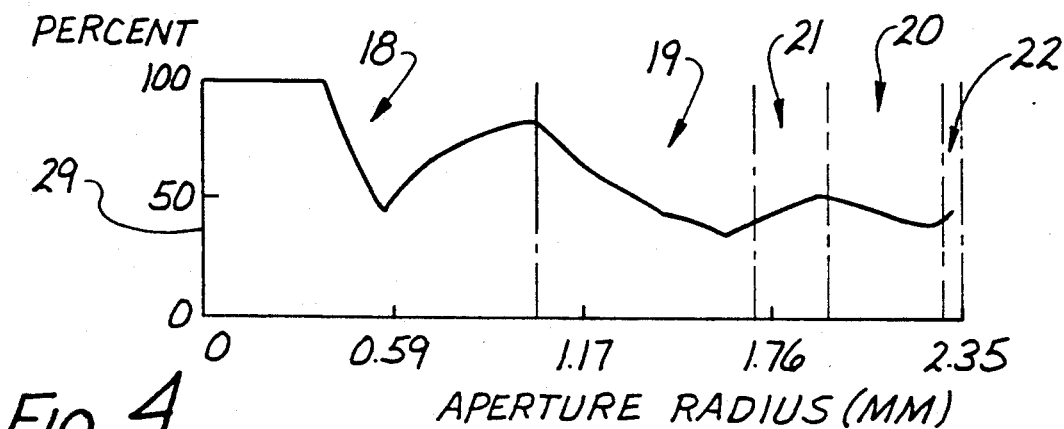
FIGS. 4-6 are plots of percent intensity contribution versus radius from the optical axis for far, near and intermediate images, respectively, for the IOL.
Figure 5:
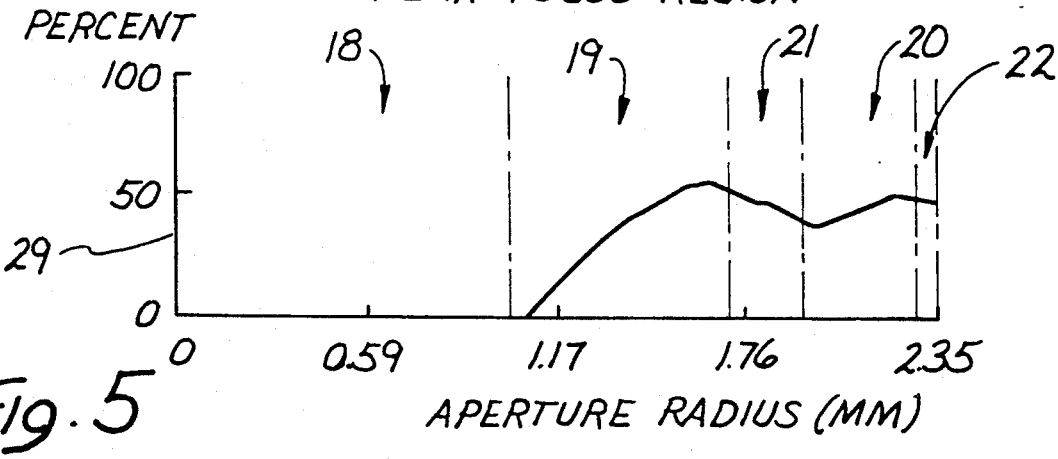
Figure 6:
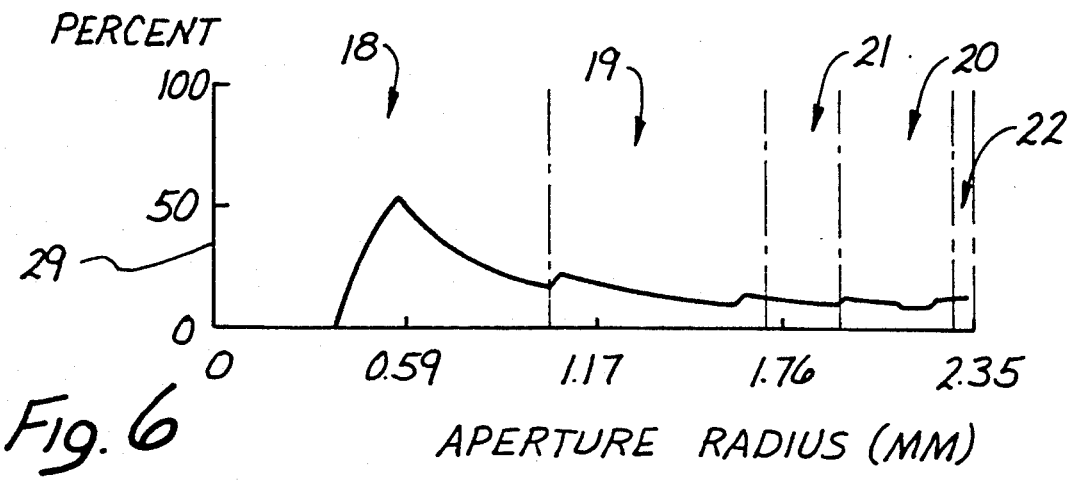

One advantage of this invention and in particular of the variation in vision correction powers is in the effective distribution of focused light intensity at far, near and intermediate focus regions. This is illustrated in FIGS. 4–6 which show the percentage of light intensity which is focussed in the far, near and intermediate focus regions, respectively, by the optic 13 for all apertures from the optical axis 29 to the periphery 37, i.e., for apertures up to 4.7 mm in diameter. In FIGS. 4–6, the zones 18–22 are separated by dashed lines, and the zone 23, which is dedicated to far vision correction under poor lighting conditions, is not shown.

Figure 3A:
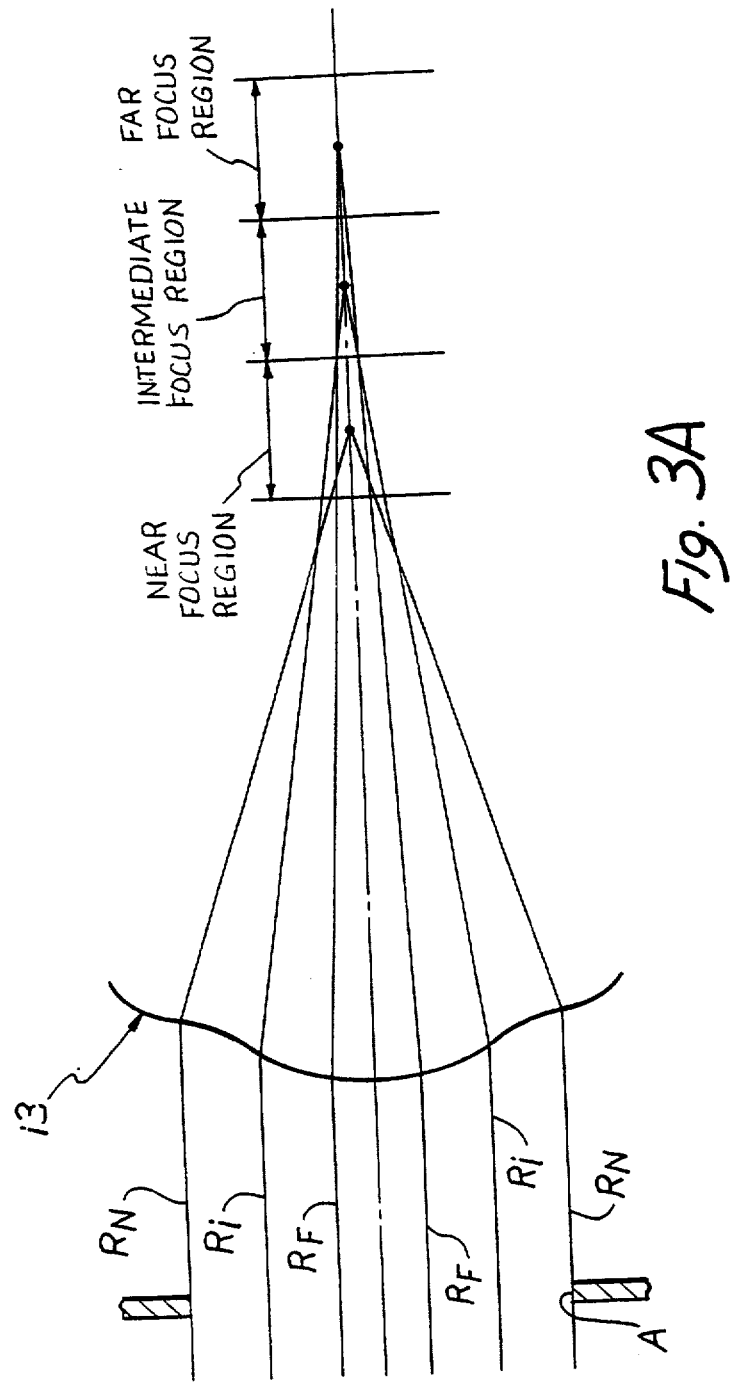
FIG. 3A is a diagrammatic view showing how the optic focuses parallel light through an aperture to a near focus region, an intermediate focus region and a far focus region.

As an aid to understanding FIGS. 4–7, FIG. 3A shows how the optic 13 focuses parallel incoming light through an aperture A to a near focus region, an intermediate focus region and a far focus region. The aperture A may be of any size out to the periphery 37, and in the form shown in FIG. 3A is about 3 mm in diameter. From FIG. 3A, it can be seen that peripheral rays $R_n$ are focussed by the optic 13 in the near focus region. With reference to FIG. 3, these are rays that are along the plateau 41. Central rays $R_f$ are focussed in the far focus region, and these rays may be, for example, in the zone 18. Finally, other rays $R_i$ are focussed by the optic 13 in the intermediate focus region, and these rays may come, for example, from the zone 18 near the apex 38 or in the intermediate range of the zone 19.

FIG. 4 shows the percent of light focussed by the optic 13 in the far focus region for any aperture size out to 4.7 mm diameter. FIGS. 5 and 6 provide the same information for light focussed in the near and intermediate focus regions, respectively. It is important to note that each point on the "X" axis of FIGS. 4–6 represents an aperture radius or area and that the "Y" axis in each of these figures represents the percent of light for that particular aperture size which is focussed in the associated region.

FIG. 4 shows a significant intensity contribution to far images at all locations on the optic 13 and that, for a significant portion of the central zone 18, 100 percent of the light intensity is focussed in the far focus region and, therefore, contributes to the far image. In this specific example, the average intensity of light focussed in the far focus region is 49 percent for an annular aperture having an inner diameter of about 2 mm and an outer diameter of about 4.7 mm. Dedicating this portion of the light to far vision is important because much of the viewing commonly done is at images requiring good far vision. Also, this is at least as great a percentage of light as the natural lens of the eye provides for far vision for an older patient.

FIG. 5 shows the percent of light intensity focussed by the optic 13 in the near region (FIG. 3A). For an annular aperture having an inner diameter of about 2 mm and an outer diameter of about 4.7 mm, the average percent of light intensity focussed by the optic 13 in a near image in this example is 37 percent. The plateaus 41 and 45 contribute significantly to focussed light intensity in the near focus region and to the relatively high intensity contribution to the near images. If the plateaus 41 and 45 were replaced with a rounded or pointed apex, the average intensity contribution to near images would be reduced. The central zone 18 makes no light intensity contribution to near images.

Finally, FIG. 6 shows by way of example an average focussed light intensity in the intermediate region and contribution to intermediate images of about 14 percent for an annular aperture having an inner diameter of about 2 mm and an outer diameter of about 4.7 mm. For apertures below 2 mm in diameter, a significant portion of the light contributes to intermediate images. All of the zones 18–22 make some intensity contribution to intermediate images, i.e., have some light focussed in the intermediate region, with the contribution of the central zone near the apex 38 being the greatest.

Figure 7:
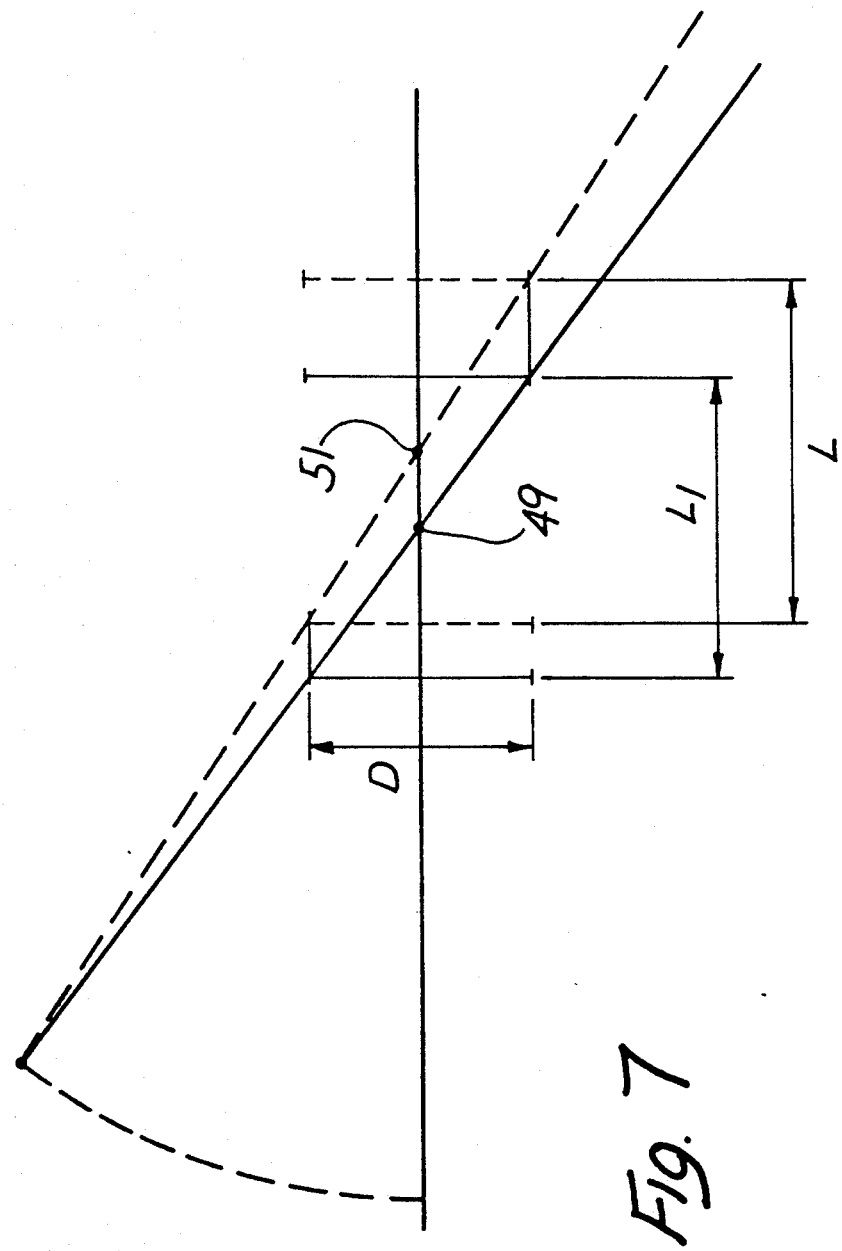
FIG. 7 is a ray diagram showing one way the depth of focus of the central zone is increased.
Figure 10:
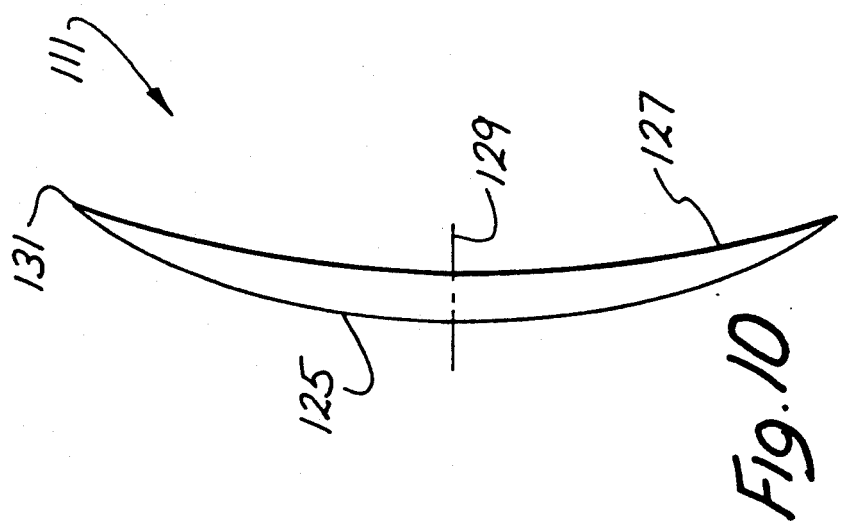
FIG. 10 is a side elevational view of the contact lens.

One advantage of the far, far vision correction powers of the central zone 18 is to increase the depth of focus of the central zone of the multifocal optic 13. The depth of focus is defined by the size of the blur spot which provides tolerable vision. In FIG. 7, a blur spot having a radial dimension "D" provides tolerable vision. FIG. 7 compares the depth of focus obtained by directing the peripheral rays to a far focal point 49 and a far, far focal point 51. Because a peripheral region of the central zone 18 has far, far vision correction powers, the rays at the periphery of the central zone are directed to the far, far focal point 51. From FIG. 7, it can be seen that directing the peripheral rays to the far, far focal point 51 provides a depth of focus "L" which is greater than the depth of focus $L_1$ provided by directing the peripheral rays to the far focal point 49. In addition, the variable vision correction powers of the central zone 18 also serve to increase the depth of focus of the central zone.

Figure 8:
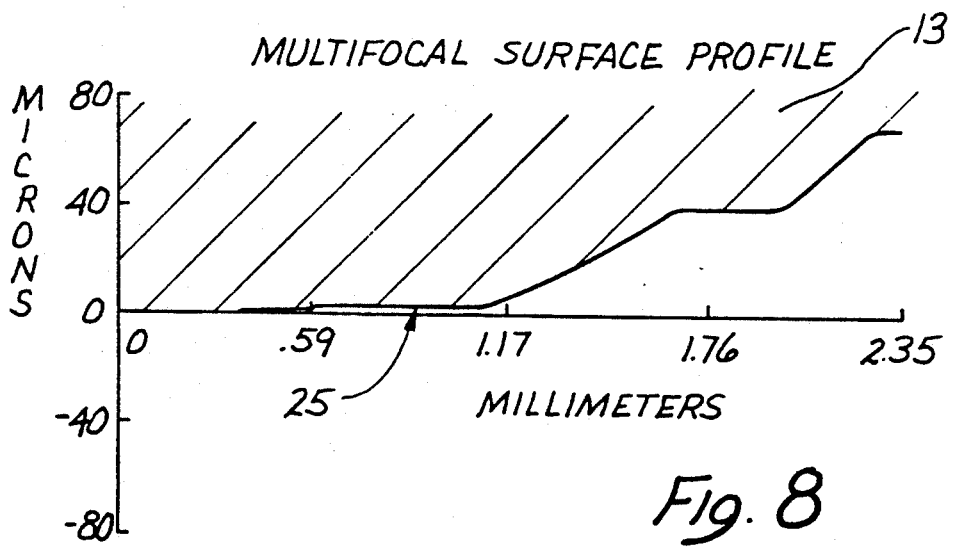
FIG. 8 is a greatly enlarged plot showing an anterior surface profile for the IOL.

FIG. 8 shows the configuration of the anterior surface 25 of the optic 13 at various distances from the optical axis 29 which can be used to provide the power curve of FIG. 3 for an optic of silicone having a refractive index of 1.408. Preferably, the anterior surface 25 has a base curve which provides the power for far vision, and this far vision correction power is considered the baseline power. The shape of the anterior surface 25 of FIG. 8 can be coordinated with the diopter powers of FIG. 3 by the numerical designations on the abcissa. The ordinate shows the depth to which the optic 13 is cut, or otherwise, formed.

The anterior surface 25 is entirely aspheric, and this is true even of the regions which correspond to the plateaus 41 and 45. It is possible to have a constant power as exemplified by the plateaus 41 and 45 utilizing an aspheric surface by varying the location of the center of the radius. This technique is explained in *Lens Design Fundamentals* by Rudolf Kingslake published by Academic Press of New York in 1978 and is known to those having ordinary skill in the art. The use of an aspheric surface minimizes spherical aberrations, and because an aspheric surface is needed for progressive portions of the lens, it can easily be employed for the entire anterior surface 25.

Ideally, a spherical surface provides constant power. However, a non-ideal spherical surface does not focus rays to the same point, thereby creating spherical aberrations. The aspheric surface 25 minimizes these aberrations.

Figure 9:
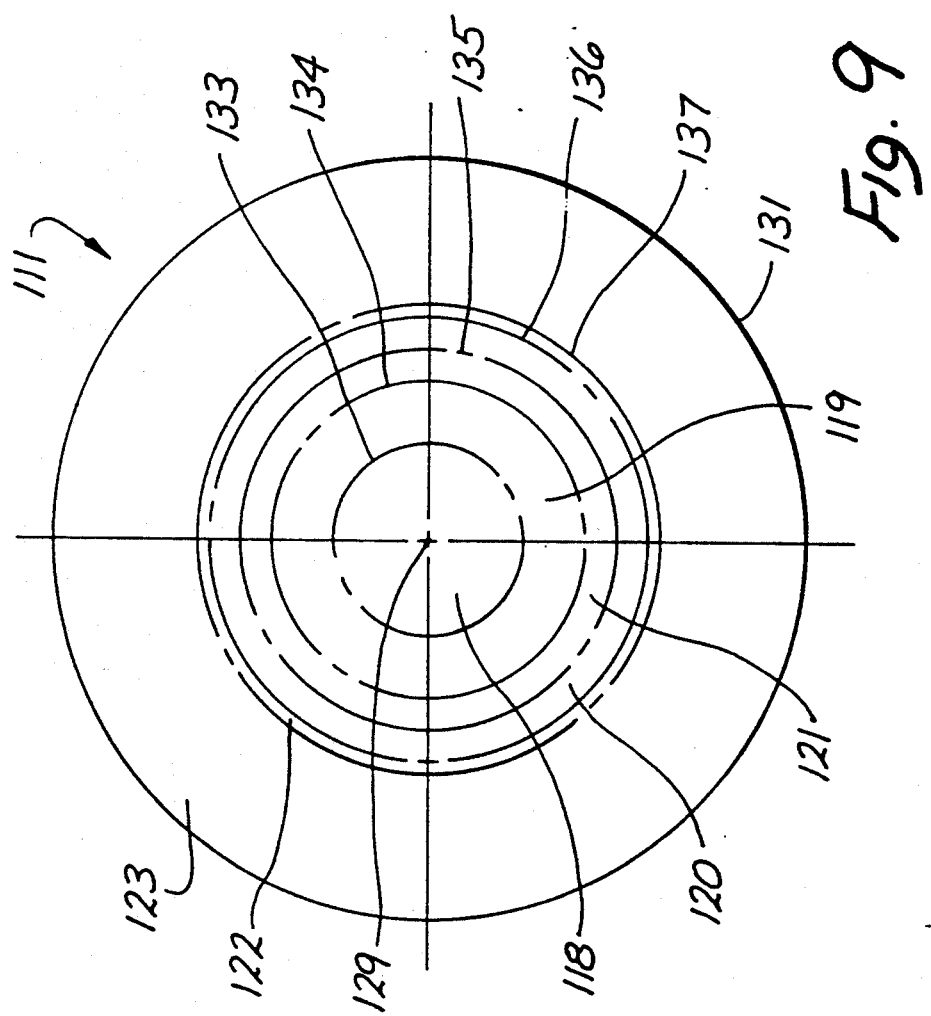
FIG. 9 is a plan view of a contact lens constructed in accordance with the teachings of this invention.

FIG. 9 shows a contact lens 111 constructed in accordance with the teachings of this invention. The contact lens 111 is sized and configured to be carried or worn on a surface of the eye. Optically, the contact lens 111 may be essentially identical to the optic 13 of FIGS. 1–8 in all respects not shown or described herein. Portions of the figures relating to the contact lens 111 which correspond to portions of the figures relating to the intraocular lens 11, are designated by corresponding reference numerals preceded by the numeral "1".

Optically, the contact lens 111 has a central zone 118, inner annular near zones 119 and 120 and outer annular zones 121–123 which correspond, respectively, to the zones 21–23 of the intraocular lens 11. The contact lens 111 has a convex anterior surface 125 which is shaped to provide the desired variable vision correction powers, and a posterior surface 127 which is concave and configured to the desired shape for the eye of the wearer. Of course, the corrective powers could be provided on the posterior surface 127, if desired.

Figure 11:
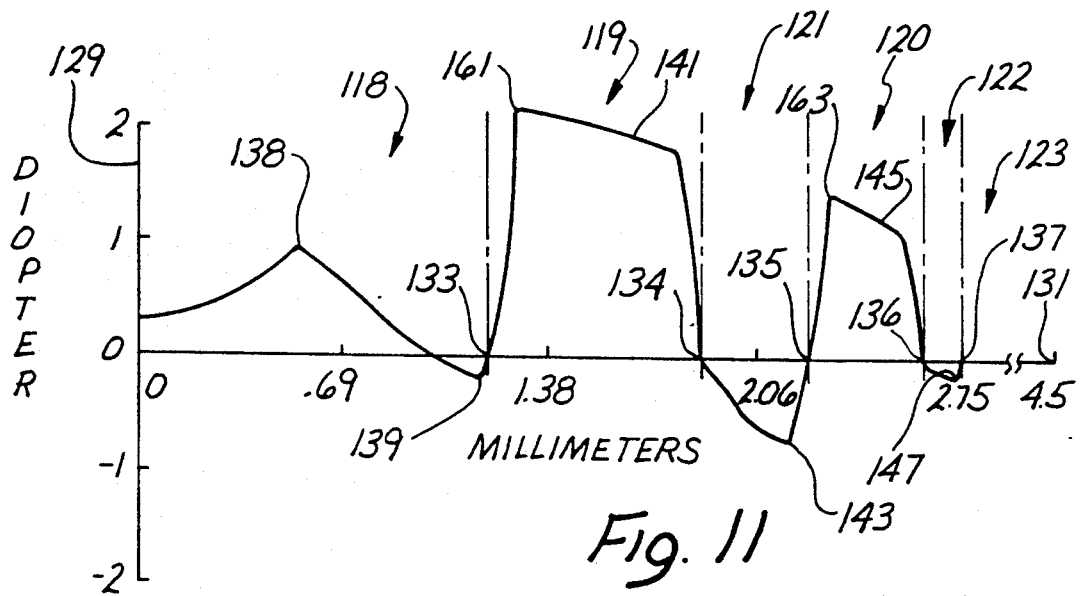
FIGS. 11-15 provide similar information for a relatively progressive contact lens that FIGS. 3-6 and 8 provide for the IOL of FIGS. 1 and 2.

Optically, the contact lens 111 is very similar to the intraocular lens 11, and this can be seen by comparing FIG. 11 with FIG. 3. The zero diopter or baseline power is the patient's prescription for far vision and, therefore, is different from patient to patient.

FIG. 11 shows the power or diopter distribution for a contact lens which is quite progressive and which includes spherical aberration compensation. In FIG. 11, the baseline power at the "X" axis represents the correction required by a particular patient for far vision correction.

A contact lens exhibits significant spherical aberration. To help correct this, the power curve of FIG. 11 is tilted downwardly in a radial outward direction. This tilt results in the power curve beginning at the optical axis 129 at some positive diopter power rather than at a negative diopter power as in the case of the IOL of FIG. 3. The IOL does not suffer from the spherical aberration problems to the same degree as a contact lens.

For the contact lens 111, the vision correction power begins with intermediate correction at the optical axis 129 and increases progressively and continuously to an apex 138 and then decreases progressively and continuously across the abcissa to the point 139 which provides a negative diopter power for far, far correction. This increases the depth of focus in that the rays at the periphery of the central zone 118 are directed to a far, far focal point as shown in FIG. 7. The apex 138 is also considered an intermediate correction power.

The central zone 118 differs from the central zone 18 in that the power at the optical axis 129 is slightly positive and may be considered as providing far vision correction powers. For a contact lens, the power shift correction provided by the far-far correction at the optical axis of the intraocular lens 11 is not used. Accordingly, the mean power of the central zone may be greater than the patient's prescription for far correction.

The inner annular near zone 119 has a continuously varying progressive vision correction power from the periphery 133 to the periphery 134 to help increase the depth of focus. The primary difference between the inner annular near zone 119 and the inner annular near zone 19 of FIG. 3 is that the plateau 141 is sloped to provide progressively reducing near vision correction powers to correct for spherical aberrations in the zone 119. The primary difference between the annular far zones 21 and 121 is that, in the zone 121, the vision correction power progresses negatively and smoothly from the periphery 134 to the point 143 to correct for spherical aberrations.

Similarly, the outer annular near zone 120, which extends from the periphery 135 to the 136 has continuously and progressively varying vision correction powers, with the plateau 145 also sloping like the plateau 141 to correct for spherical aberrations in the zone 120. Thus, in the annular near zones 119 and 120, the vision correction power increases in a radial outward direction and relatively rapidly from a far vision correction power at the peripheries 133 and 135 to a maximum near vision correction power at locations 161 and 163, respectively, and then decreases in a radial outward direction more slowly during a major segment of the near vision region, i.e., the plateaus 141 and 145. Finally, the vision correction power decreases in a radial outward direction more rapidly from the radial outer ends of the plateaus 141 and 145 to the peripheries 134 and 136, which represent a far vision correction power. However, the plateaus 141 and 145 serve, similar to the plateaus 41 and 45 (FIG. 3), to somewhat concentrate light for near vision viewing and to provide somewhat sharpened near vision images.

The annular zone 122 provides a vision correction power which decreases radially outwardly from the periphery 136 almost to the periphery 137 where it returns progressively to the axis at the periphery 137. The zone 123, like the zone 23, extends from the periphery 137 to the outer periphery 131 and provides far vision correction under poor light conditions. The radial dimensions of the zones 118–123 are different from the corresponding radial dimensions of the zones 18–23, as shown by comparing FIGS. 11 and 3. For example, the diameter of the contact lens 111 may be from about 9 mm to about 13 mm.

Sloping the plateaus 141 and 145, as well as regions of the zones 121 and 122, is useful in reducing aberrations in each of the zones. The sloping of the power curve in the far zones 121 and 122 reduces the power in these zones into the far, far range. As a result of this overall sloping of the power curve, the maximum vision correction power at the location 161 in the near zone 119 is greater than maximum vision correction power at the location 163 of the near zone 120.

Figure 12:
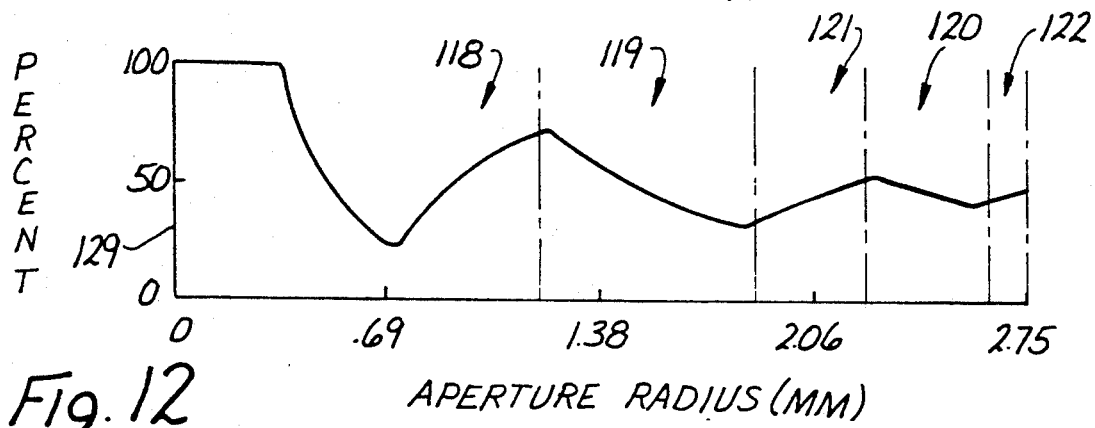
Figure 13:
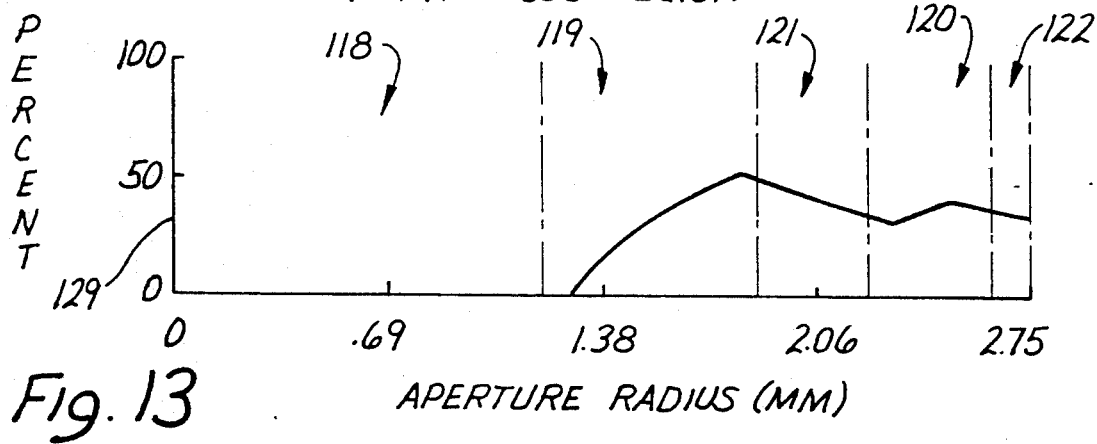
Figure 14:
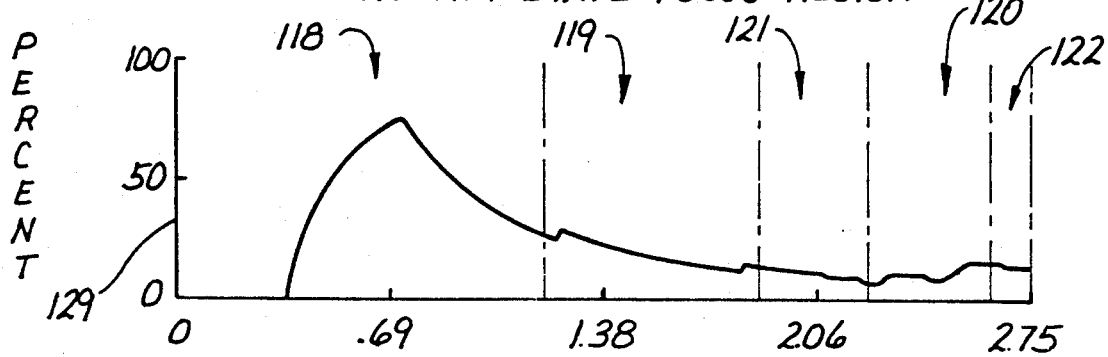

FIGS. 12–14 show the focussed light intensity in the far, near and intermediate focus regions, respectively, and therefore correspond to FIG. 4–6. For contact lenses, apertures above 5.5 mm typically occur only in dim light where far vision dominates. The zones 118–123 are separated by dashed lines in FIGS. 12–14. In this embodiment, the contact lens 111 achieves an average intensity of focussed light in the far focus region of 48 percent, an average intensity of focussed light in the near focus region of 34 percent, and an average intensity of focussed light in the intermediate focus region of 18 percent for annular apertures having an inner diameter of about 2.25 mm and an outer diameter of about 5.5 mm. Accordingly, the light intensity is very effectively utilized for far and near images in addition to providing extended depth of focus in the central zone 118 to compensate for the absence of near power correction in the central zone.

The curves of FIGS. 12–14 are quite similar to the curves of FIGS. 4–6, respectively. For example 100 percent of the light in the region around the optical axis 129 contributes to intensity of focussed light in the far focus region, i.e., to the intensity of the far image, and none of the light in the central zone 118 contributes to the near image. The intermediate light intensity is highest in the central zone 118 and reduces smoothly at locations radially outwardly of the central zone 118.

Figure 15:
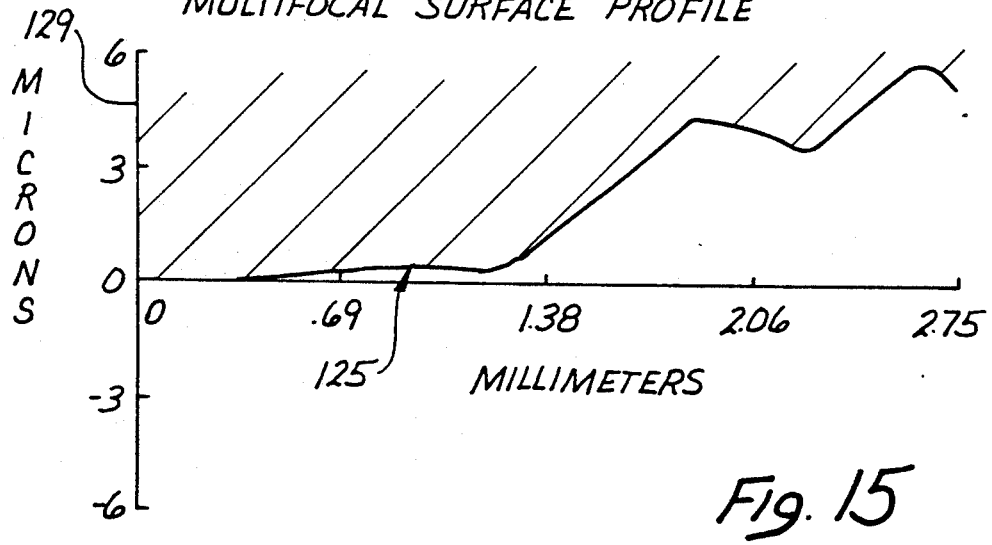

FIG. 15 shows one way in which the anterior surface 125 of the contact lens 111 may be shaped to provide the variable vision correction powers of FIG. 11 for an optic of polymacon having a refractive index of 1.443. The contact lens 111 has a base curve which provides a zero diopter or baseline power for far vision correction power, and this zero diopter or baseline power corresponds to the patient's prescription for far vision. The base curve is modified to provide the vision correction powers of FIG. 11. The anterior surface 125 is preferably aspheric throughout.

Figure 16:
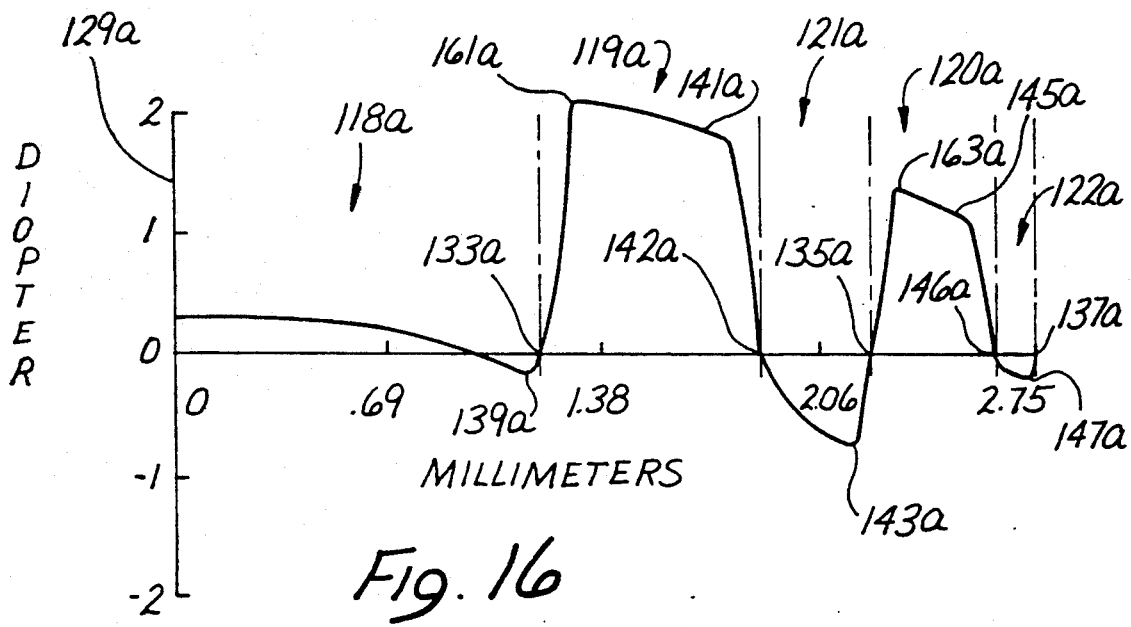
FIG. 16 shows an alternate power distribution curve for a less progressive contact lens.

FIG. 16 shows an alternate surface diopter distribution for the contact lens 111. Preferred power distribution curves for a corneal onlay may be similar, or identical, to the curves of FIGS. 11 and 16. As compared with the embodiment of FIGS. 9–15, this embodiment has enhanced bifocal images with only a slightly reduced depth of focus. Conversely, the embodiment of FIGS. 9–15 provides a greater depth of focus. Portions of the curves shown in FIGS. 16–20 corresponding to portions of the curves shown in FIGS. 11–15 are designated by corresponding reference numerals followed by the letter "a".

Figure 17:
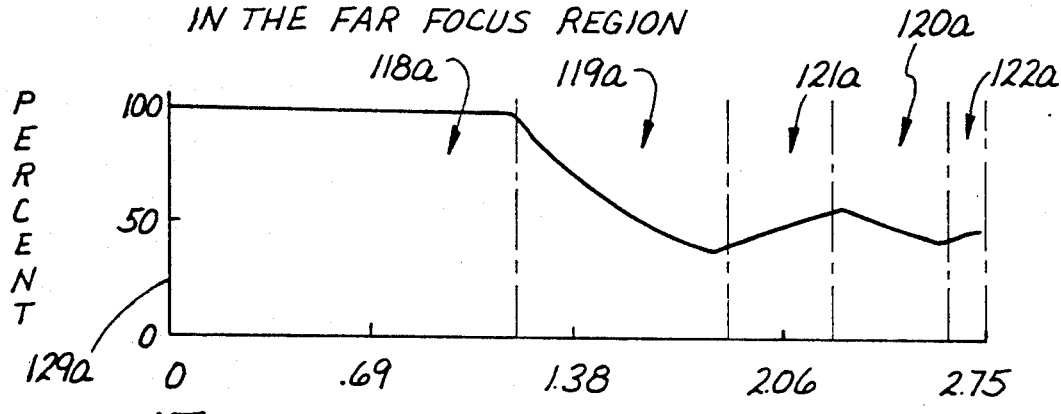
Figure 18:
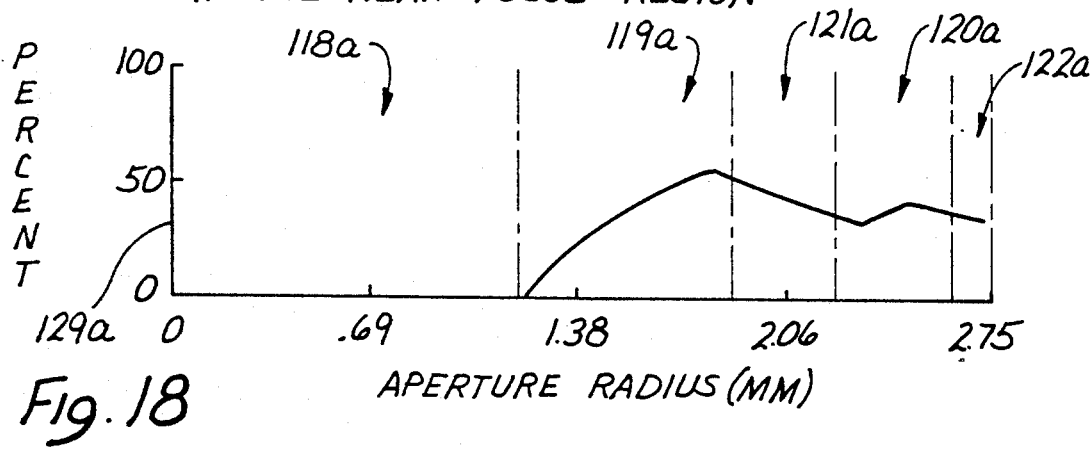
Figure 19:
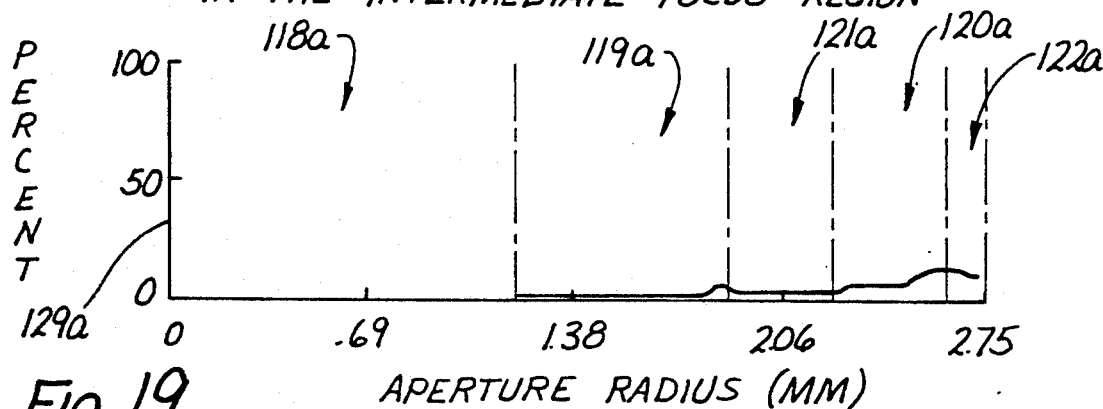

The effect of this different power distribution is shown in FIGS. 17, 18 and 19 where it can be seen that higher intensity contribution to far images is obtained. Specifically, the average intensity of focussed light in the far focus region or the average contribution to far images utilizing the power distribution of FIG. 16 is 57 percent for annular apertures having an inner diameter of about 2.25 mm and an outer diameter of about 5.5 mm. For the same annular aperture, the average intensity contribution to near images is 38 percent, and the average intensity contribution to intermediate images is only 4 percent. Thus, the power distribution of FIG. 16 can be used where substantial light intensity is desired for far images while maintaining good light intensity for near images and a more modest light intensity for intermediate images.

In FIG. 16, the central zone 118a extends to the periphery 133a. The vision correction power begins with a far vision correction power at the optical axis 129a and decreases continuously and progressively within the range of far vision correction powers to a point 139a in the far, far range and then returns to zero diopter power at the periphery 133a. Consequently, the rays at the periphery of the central zone 118a are directed to a far, far focal point as shown in FIG. 7 to provide an increased depth of focus for the central zone. However, the central zone 118a has somewhat less progressive vision correction powers than the central zone 118 (FIG. 11), and to that extent, does not have as great a depth of focus as the central zone 118. All of the light intensity from the optical axis 129a to the periphery 133a, i.e., in the central zone 118a, is devoted to the far image as shown in FIG. 17. The mean vision correction power of the central zone 118a is slightly greater than the zero diopter or baseline vision correction power.

Figure 20:
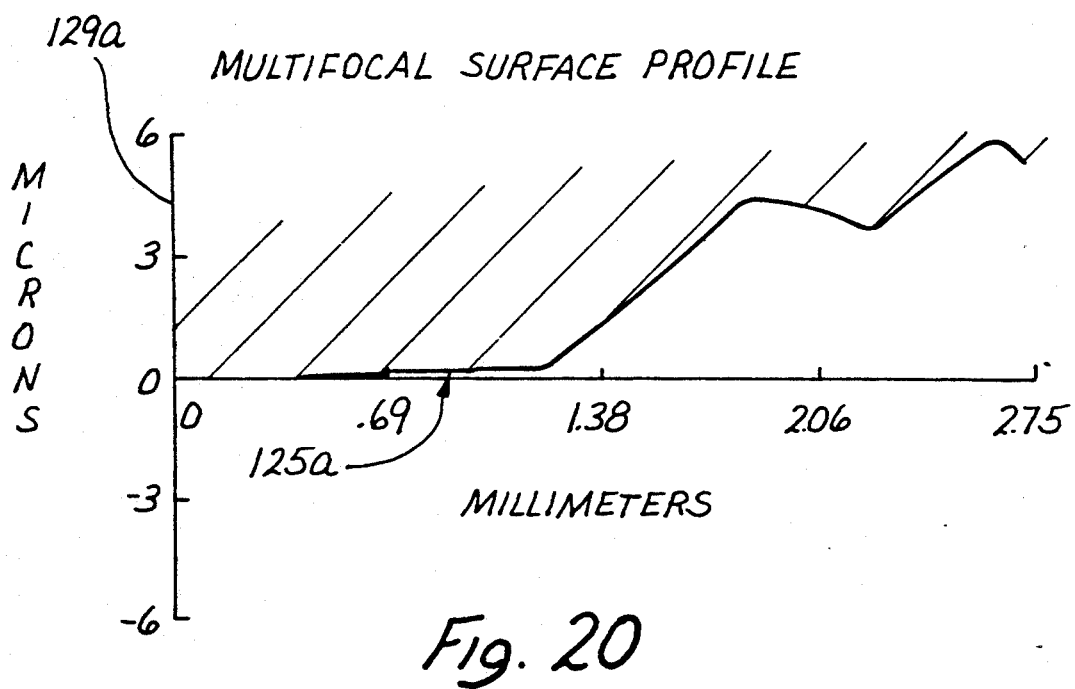
FIGS. 17-20 provide the same information for the alternate power distribution embodiment of FIG. 16 that FIGS. 12-15 provide for the power distribution curve of FIG. 11.

From the periphery 133a radially outwardly, the curve of FIG. 16 may be substantially identical to the curve of FIG. 11. The differences in the light intensity curves of FIGS. 17–19 and 12–14 are due primarily to the differences in the vision correction powers of the central zones 118a and 118. The anterior surface of a contact lens which is to have the vision correction powers of FIG. 16 can be shaped as discussed above in connection with FIG. 15. FIG. 20 shows by way of example how the anterior surface 125a of the contact lens may be shaped to provide the variable vision correction powers of FIG. 16.

Although exemplary embodiments of the invention have been shown and described, many changes, modifications and substitutions may be made by one having ordinary skill in the art without necessarily departing from the spirit and scope of this invention.

I claim:

1. A multifocal ophthalmic lens for providing vision correction powers, said lens being adapted for implantation in an eye or to be disposed on or in the cornea, said lens having a baseline diopter power for far vision correction power, said lens having a central zone and a first outer zone radially outwardly of the central zone, said central zone having a progressive power region in which the vision correction powers vary progressively and in radially outwardly extending order from an intermediate vision correction power, to a far vision correction power and then to a diopter power which is less than the baseline diopter power.

2. A lens as defined in claim 1 wherein the lens has anterior and posterior surfaces with one of said surfaces being configured to provide said vision correction powers, said one surface having a base curve defining said baseline diopter power for far vision correction power.

3. A lens as defined in claim 1 wherein the vision correction powers of the central zone are continuously variable.

4. A lens as defined in claim 1 wherein the lens has an optical axis extending through the central zone and the vision correction power increases from the optical axis to said intermediate vision correction power.

5. A lens as defined in claim 4 wherein the vision correction power at the optical axis is less than the baseline diopter power.

6. A lens as defined in claim 1 wherein the mean power in the central zone is about the baseline diopter power.

7. A lens as defined in claim 1 wherein the central zone is no greater than about 2.25 mm in diameter, the first outer zone is contiguous the central zone and has a far vision correction power adjacent the central zone and a region having a near vision correction power, the vision correction power of the first outer zone between the far and near vision correction powers being progressive.

8. A lens as defined in claim 1 wherein the intermediate vision correction power is the greatest diopter power of the central zone.

9. A lens as defined in claim 8 wherein the lens has an optical axis extending through the central zone and the vision correction power increases from the optical axis to said intermediate vision correction power, and the vision correction power at the optical axis is less than the baseline diopter power.

10. A lens as defined in claim 1 wherein the diopter power which is less than the baseline power is in an outer peripheral region of the central zone.

11. A lens as defined in claim 1 wherein the first outer zone is annular and circumscribes the central zone.

12. A lens as defined in claim 11 wherein the first outer zone has a far vision correction power adjacent the central zone and a region having a near vision correction power, the vision correction power of the first outer zone between the far and near vision correction powers being progressive.

13. A lens as defined in claim 12 including a second outer zone which is annular and circumscribes the first outer zone, said second outer zone has a far vision correction power and a region having a near vision correction power, and the vision correction power between the far and near vision correction powers of the second outer zone is progressive.

14. A lens as defined in claim 13 wherein each of said regions has a major segment in which the near vision correction power is substantially constant.

15. A lens as defined in claim 14 wherein the lens has a third annular zone between the first and second annular zones, said third annular zone being for far vision.

16. A multifocal ophthalmic lens for providing variable vision correction power, said lens being adapted for implantation in an eye or to be disposed on or in the cornea, said lens having an optical axis, said lens having a plurality of annular zones circumscribing the optical axis, each of first and second of said annular zones having a far vision correction power and a region having a near vision correction power, the vision correction power between the far and near vision correction powers being progressive, each of said regions having a major segment in which the near vision correction power is substantially constant, the lens having a central zone circumscribed by the annular zones, said central zone having a progressive vision correction power which is less than near vision correction power throughout the full radial dimension of the central zone.

17. A lens as defined in claim 16 wherein the lens has a third annular zone extending between the first and second annular zones, said third zone having a vision correction power which is less than near vision correction power throughout the full radial dimension of the third annular zone.

18. A lens as defined in claim 17 wherein the third annular zone has a major segment with a far vision correction power which varies.

19. A lens as defined in claim 17 wherein each of the first and second annular zones has far vision correction powers on opposite sides of said region of such zone and the vision correction power is progressive between said region and the far vision correction powers on the opposite sides of said region.

20. A lens as defined in claim 16 wherein a first of the major segments lies radially inwardly of a second of the major segments and has a greater radial dimension than the second major segment.

21. A lens as defined in claim 16 wherein the lens has an anterior surface and a posterior surface and one of said surfaces has an aspheric section providing the near vision correction power for at least a portion of one of said major segments.

22. A lens as defined in claim 21 wherein said one surface is aspheric throughout said annular zones.

23. A lens as defined in claim 16 wherein the central zone has intermediate and far vision correction powers and the progressive vision correction power of the central zone blends the intermediate and far vision correction powers of the central zone.

24. A lens as defined in claim 16 wherein said central zone has a vision correction power which varies in a radial outward direction from a far vision correction power to an intermediate vision correction power to a far vision correction power, the intermediate vision correction power being the maximum vision correction power of the central zone.

25. A multifocal ophthalmic lens for providing variable vision correction power, said lens being adapted for implantation in an eye or to be disposed on or in a surface of the cornea, said lens having an optical axis and a plurality of annular zones circumscribing the optical axis, each of at least said first and second annular zones having a region with a near vision correction power, the vision correction power in each of said first and second annular zones increasing in a radial outward direction and relatively rapidly from a far vision correction power to a maximum near vision correction power, then decreasing in a radial outward direction more slowly during at least a major segment of said region and then decreasing in a radial outward direction more rapidly to a far vision correction power, the second annular zone circumscribing the first annular zone.

26. A lens as defined in claim 25 wherein said lens has a baseline diopter power for far vision correction power and a diopter vision correction power between said first and second zones which is less than the baseline diopter power.

27. A lens as defined in claim 25 wherein the maximum vision correction power of the region of one of said zones is greater than the maximum vision correction power of the region of the zone which lies immediately radially outwardly of said first zone.

28. A lens as defined in claim 25 wherein the lens has an anterior surface and a posterior surface and one of said surfaces has an aspheric section providing the near vision correction power for at least a portion of one of said major segments.

29. A lens as defined in claim 25 wherein the lens has a third annular zone between the first and second annular zones, said third annular zone being for far vision and having vision correction powers which decrease for a distance radially outwardly of the first annular zone.

30. A lens as defined in claim 29 wherein the lens has a baseline diopter power for far vision and the vision correction powers of the third annular zone in said distance includes a diopter power which is less than the baseline diopter power.

31. A lens as defined in claim 25 wherein the lens has a central zone which is circumscribed by the annular zones, the central zone has far vision correction powers which decrease radially outwardly in at least a portion of the central zone.

32. A lens as defined in claim 31 wherein the lens has a baseline diopter power for far vision and the vision correction powers of the central zone include a diopter power which is less than the baseline diopter power in said portion of said central zone.

33. A multifocal ophthalmic lens for providing variable vision correction power, said lens adapted for implantation in an eye or to be disposed on or in a surface of the cornea, said lens having a baseline diopter power for far vision correction power, said lens having a central zone and a first outer zone radially outwardly of the central zone, said central zone having a peripheral region with a negative diopter power which is less than the baseline diopter power whereby the depth of focus of the central zone is increased.

34. A lens as defined in claim 33 wherein the first outer zone is annular, contiguous the central zone and circumscribes the central zone, the first outer zone having vision correction powers which include a near vision correction power.

* * * * *

UNITED STATES PATENT AND TRADEMARK OFFICE
CERTIFICATE OF CORRECTION

PATENT NO. : 5,225,858
DATED : July 6, 1993
INVENTOR(S) : Valdemar Portney

It is certified that error appears in the above-indentified patent and that said Letters Patent is hereby corrected as shown below:

Add the Drawing Sheet, consisting of Fig.3A, as shown on the attached pages.

Signed and Sealed this

Twenty-ninth Day of November, 1994

Attest:

BRUCE LEHMAN

Attesting Officer     Commissioner of Patents and Trademarks